(12) United States Patent
Dewey et al.

(10) Patent No.: US 11,986,228 B2
(45) Date of Patent: *May 21, 2024

(54) SURGICAL INJECTION SYSTEM AND METHOD

(71) Applicant: Warsaw Orthopedic, Inc., Warsaw, IN (US)

(72) Inventors: Jonathan M. Dewey, Memphis, TN (US); Anthony J. Melkent, Germantown, TN (US); William D. Armstrong, Memphis, TN (US); Daniel A. Shimko, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 333 days.

This patent is subject to a terminal disclaimer.

(21) Appl. No.: 17/333,824

(22) Filed: May 28, 2021

(65) Prior Publication Data
US 2021/0282825 A1 Sep. 16, 2021

Related U.S. Application Data

(62) Division of application No. 15/076,096, filed on Mar. 21, 2016, now Pat. No. 11,020,160.

(51) Int. Cl.
*A61B 17/88* (2006.01)
*A61B 17/00* (2006.01)
(Continued)

(52) U.S. Cl.
CPC .... *A61B 17/8825* (2013.01); *A61B 17/00491* (2013.01); *A61B 17/3472* (2013.01);
(Continued)

(58) Field of Classification Search
CPC .......... A61B 17/8225; A61B 17/8811; A61M 5/1405; A61M 5/1407; A61F 2/4601
See application file for complete search history.

(56) References Cited

U.S. PATENT DOCUMENTS 4,767,026 A    8/1988  Keller et al.
5,033,650 A *  7/1991  Colin ................ B05C 17/00593
                                                  285/361

(Continued)

FOREIGN PATENT DOCUMENTS

JP    2001-276099    10/2001
JP    2004-344639    12/2004
(Continued)

OTHER PUBLICATIONS

1 Korean Intellectual Property Office (KIPO), Korean Patent Application No. 10-2018-7029391, Office Action dated May 9, 2021.
(Continued)

*Primary Examiner* — Jenna Zhang
(74) *Attorney, Agent, or Firm* — Sorell, Lenna & Schmidt, LLP

(57) ABSTRACT

A surgical injection device includes at least one tubular element defining a passageway. The passageway is configured for disposal of a selected volume of an agent and an evacuator disposed within the passageway. An actuator is engageable with the evacuator to entirely expel the selected volume of the agent from the passageway to a selected site. Spinal constructs, implants, systems and methods are disclosed.

16 Claims, 12 Drawing Sheets

(51) Int. Cl.
  *A61B 17/34* (2006.01)
  *A61F 2/46* (2006.01)
  *A61M 5/14* (2006.01)
  *A61M 5/145* (2006.01)
  *A61M 5/19* (2006.01)

(52) U.S. Cl.
  CPC ...... *A61B 17/8805* (2013.01); *A61B 17/8811* (2013.01); *A61B 17/8816* (2013.01); *A61B 17/8819* (2013.01); *A61B 17/8822* (2013.01); *A61F 2/4601* (2013.01); *A61M 5/1407* (2013.01); *A61M 5/145* (2013.01); *A61M 5/19* (2013.01); *A61B 2017/8838* (2013.01); *A61F 2/4611* (2013.01)

(56) References Cited

U.S. PATENT DOCUMENTS

| | | |
|---|---|---|
| 5,047,031 A | 9/1991 | Constantz |
| 5,525,148 A | 6/1996 | Chow et al. |
| 5,650,108 A | 7/1997 | Nies et al. |
| 5,795,922 A | 8/1998 | Demian et al. |
| 5,820,632 A | 10/1998 | Constantz et al. |
| 5,830,193 A | 11/1998 | Higashikawa |
| 6,083,264 A | 7/2000 | Wood et al. |
| 6,479,565 B1 | 11/2002 | Stanley |
| 6,547,866 B1 | 4/2003 | Edwards et al. |
| 7,118,378 B1* | 10/2006 | Karapetyan .......... A61C 8/0009 604/181 |
| 2005/0197422 A1 | 9/2005 | Mayadunne et al. |
| 2006/0096138 A1 | 5/2006 | Truckai et al. |
| 2006/0122614 A1 | 6/2006 | Truckai et al. |
| 2006/0122625 A1* | 6/2006 | Truckai .............. A61B 17/8805 606/94 |
| 2006/0264964 A1 | 11/2006 | Scifert et al. |
| 2007/0010824 A1* | 1/2007 | Malandain ......... A61B 17/8822 606/92 |
| 2007/0191781 A1* | 8/2007 | Richards .......... A61B 17/00491 604/82 |
| 2008/0172059 A1* | 7/2008 | Trieu ................ A61B 17/8833 606/92 |
| 2010/0168868 A1* | 7/2010 | Okano .................... A61L 27/32 264/642 |
| 2010/0262245 A1 | 10/2010 | Alfaro et al. |
| 2011/0106054 A1 | 5/2011 | Osborne et al. |
| 2011/0160737 A1 | 6/2011 | Steffen et al. |
| 2013/0116657 A1* | 5/2013 | Hallahan ................. A61M 5/19 604/514 |
| 2013/0184827 A1* | 7/2013 | Lynn ....................... A61F 2/447 623/17.16 |
| 2014/0046335 A1* | 2/2014 | Mazzuca ........... A61B 17/8822 606/94 |
| 2014/0058252 A1* | 2/2014 | Varav ................. A61M 1/7415 604/28 |
| 2014/0228745 A1* | 8/2014 | Sharma ............... A61M 5/1409 604/82 |

FOREIGN PATENT DOCUMENTS

| | | |
|---|---|---|
| JP | 2004344639 A | 12/2004 |
| JP | 2019-511290 A | 4/2019 |
| WO | 20130141188 A1 | 9/2013 |
| WO | 2017/165214 A1 | 9/2017 |

OTHER PUBLICATIONS

International Search Report and Written Opinion for PCT/2017/022886, the counterpart application dated Jun. 28, 2017, 13 pages.
Extended European Search Report of the European Patent Office dated Oct. 31, 2019 issued in European Application No. 17770858.3 for Surgical Injection System and Method, filed on Mar. 17, 2017.
Notice of Reasons for Rejection (Office Action) dated Jul. 31, 2020, issued by the Japan Patent Office in corresponding Japanese application No. 2018-548364 (English translation provided).
Office Action dated Nov. 20, 2020 issued by the China National IP Administration in corresponding Chinese patent application No. 201780017212.2, English translation provided.
Office Action dated Nov. 2, 2021 by the Japan Patent Office in corresponding Japanese Appl. No. 2021-009455. English translation provided.

* cited by examiner

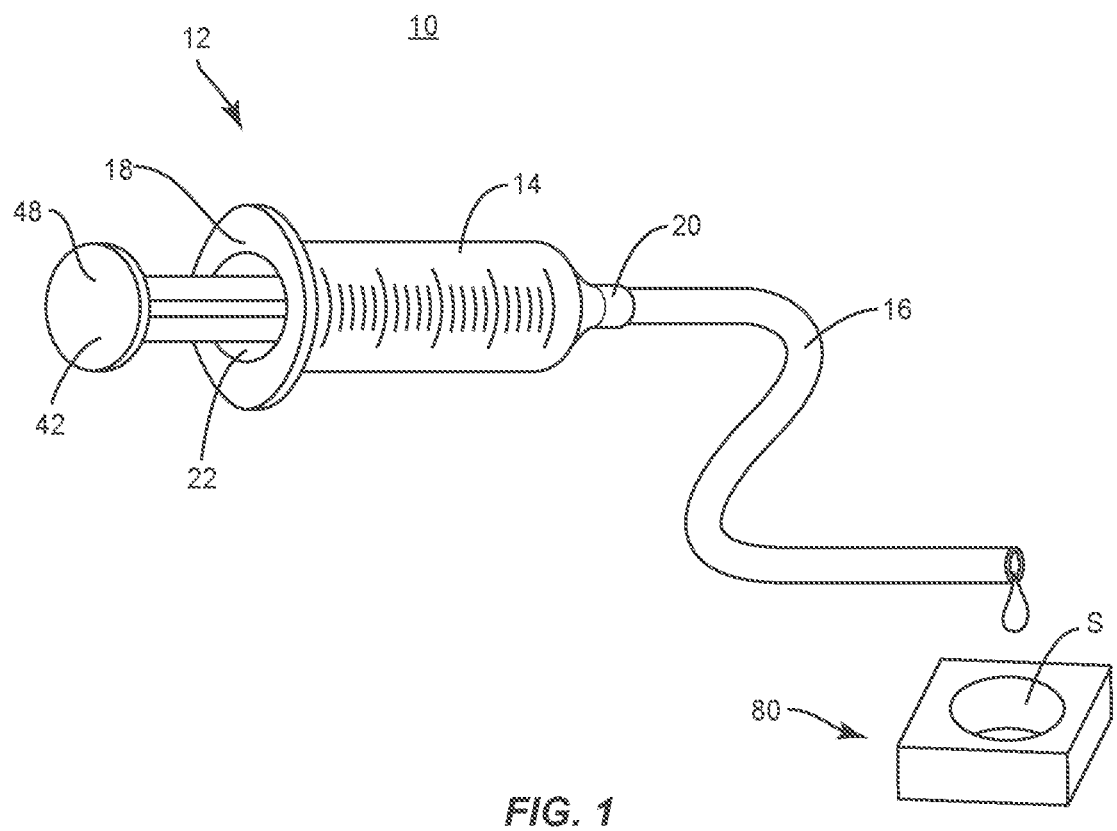
FIG. 1
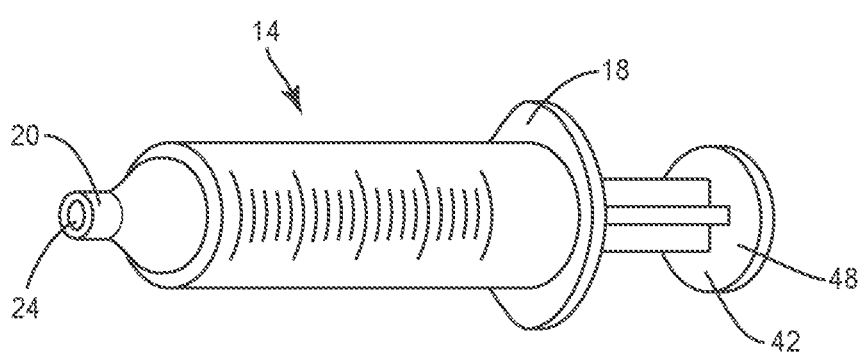
FIG. 2
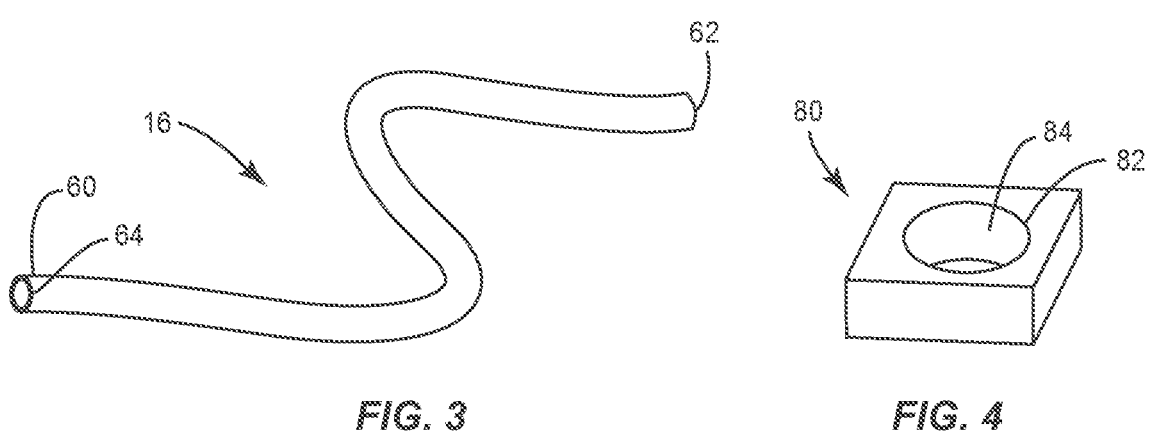
FIG. 3                    FIG. 4

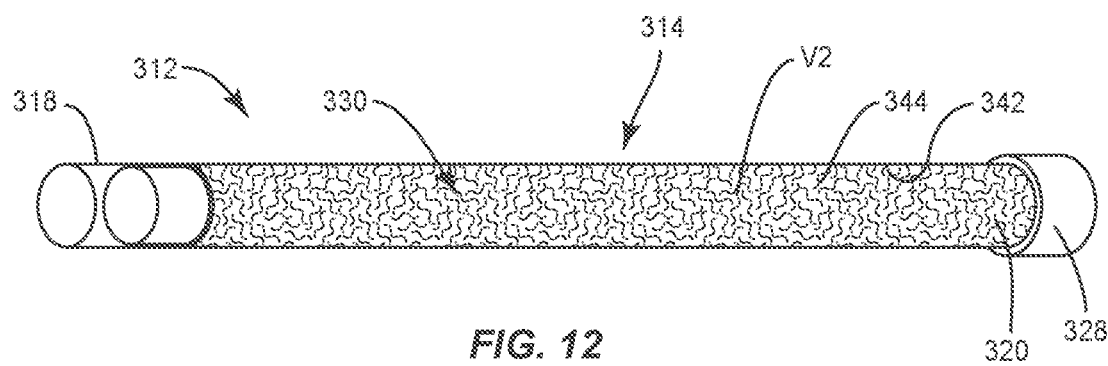
FIG. 12
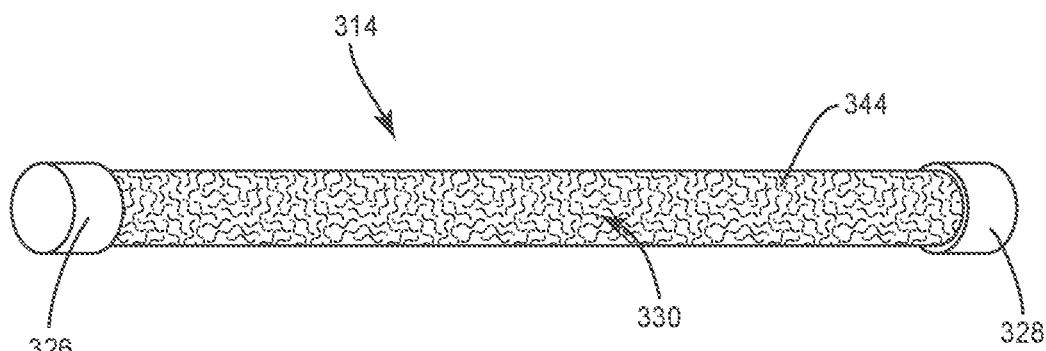
FIG. 13
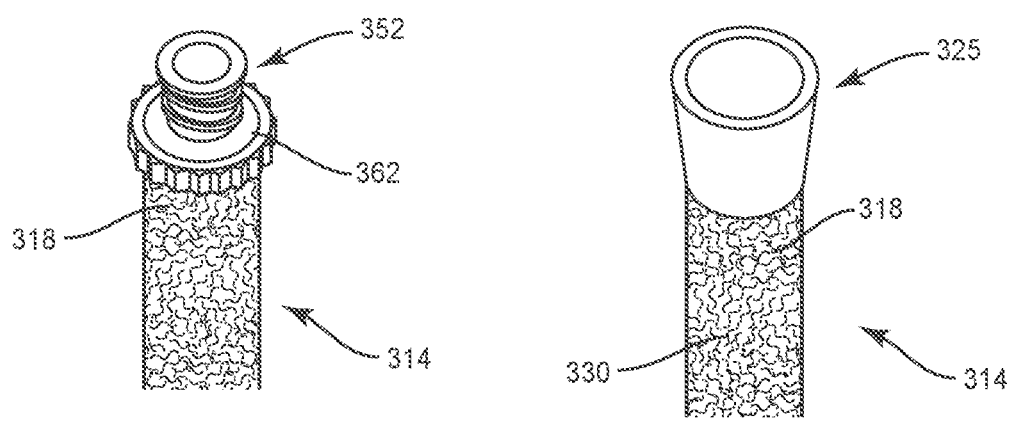
FIG. 14
FIG. 15

SURGICAL INJECTION SYSTEM AND METHOD

TECHNICAL FIELD

The present disclosure generally relates to medical devices for the treatment of musculoskeletal disorders, and more particularly to a surgical system and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. As part of these surgical treatments, spinal constructs including implants, such as, for example, bone graft, bone fasteners, spinal rods and interbody devices can be delivered to a surgical site for fixation with bone to immobilize a joint. The spinal constructs can be used to provide stability to a treated region and facilitate healing. This disclosure describes an improvement over these technologies.

SUMMARY

In one embodiment, a surgical injection device is provided. The surgical injection device includes at least one tubular element defining a passageway. The passageway is configured for disposal of a selected volume of an agent and an evacuator disposed within the passageway. An actuator is engageable with the evacuator to entirely expel the selected volume of the agent from the passageway to a selected site. In some embodiments, spinal constructs, implants, systems and methods are disclosed.

BRIEF DESCRIPTION OF THE DRAWINGS

The present disclosure will become more readily apparent from the specific description accompanied by the following drawings, in which:

FIG. 1 is a perspective view of components of one embodiment of a surgical system in accordance with the principles of the present disclosure;

FIG. 2 is a perspective view of components of the system shown in FIG. 1;

FIG. 3 is a perspective view of a component of the system shown in FIG. 1;

FIG. 4 is a perspective view of a component of the system shown in FIG. 1;

FIG. 12 is a perspective view of components of one embodiment of a surgical system in accordance with the principles of the present disclosure;

FIG. 13 is a perspective view of components of one embodiment of a surgical system in accordance with the principles of the present disclosure;

FIG. 14 is a break away view of components of one embodiment of a surgical system in accordance with the principles of the present disclosure;

FIG. 15 is a break away view of components of one embodiment of a surgical system in accordance with the principles of the present disclosure;

DETAILED DESCRIPTION

Figure 5:
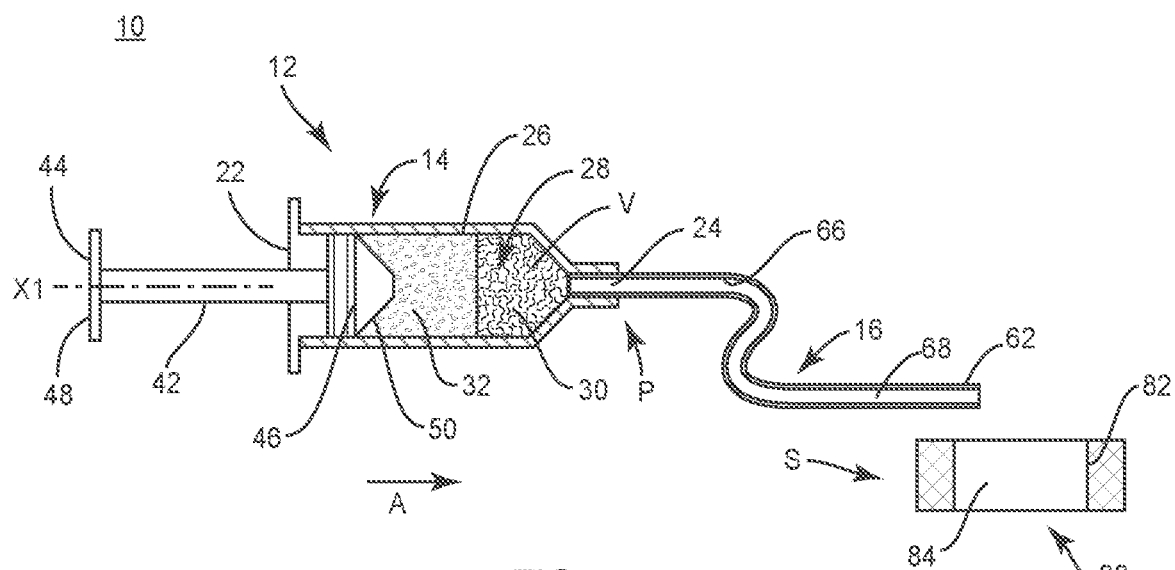
FIG. 5 is a cross section view of components of one embodiment of a surgical system in accordance with the principles of the present disclosure.
Figure 6:
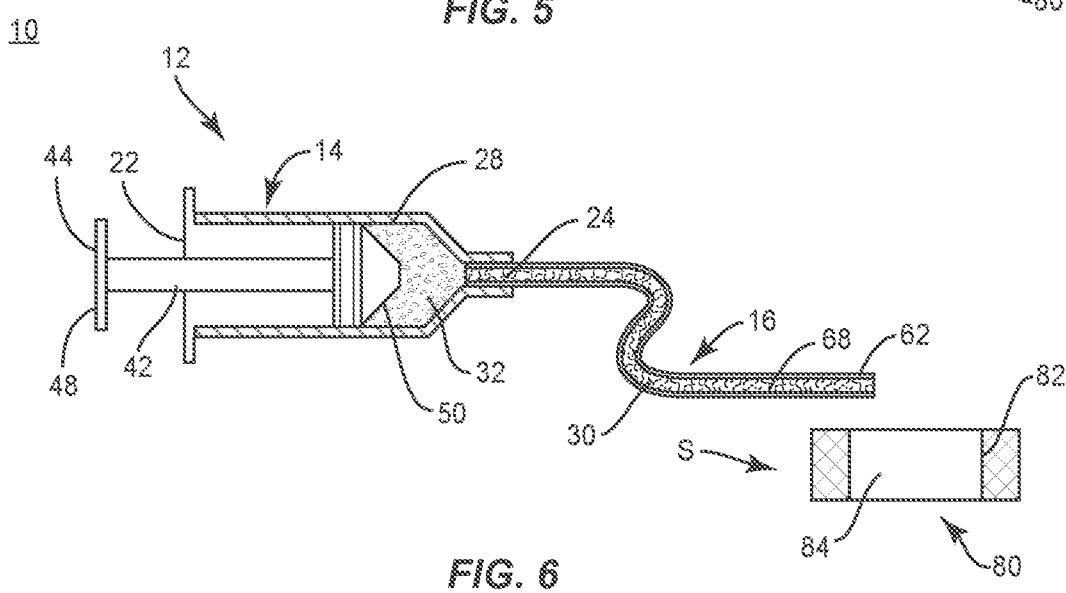
FIG. 6 is a cross section view of the components shown in FIG. 5.

The exemplary embodiments of the surgical system and related methods of use disclosed are discussed in terms of medical devices for the treatment of musculoskeletal disorders and more particularly, in terms of a surgical system and a method for treating a spine.

In some embodiments, the surgical system includes a surgical injection device, such as, for example, a syringe. In some embodiments, the surgical injection device includes a selected amount of an agent, such as, for example, bone graft material and an amount of a evacuator, such as, for example, a flowable backfill material. In some embodiments, the backfill material is configured to facilitate complete evacuation of the bone graft material from the syringe. In some embodiments, the syringe is configured for attachment with a cannula. In some embodiments, the syringe is configured for attachment with a lumen, such as, for example, a tube. In some embodiments, the backfill material is packed behind the bone graft material in a series configuration with the syringe. In some embodiments, the backfill material is configured to facilitate filling of a lumen with bone graft material and facilitates full evacuation of the bone fill material from the lumen into a surgical site and/or an implant.

In some embodiments, the surgical injection device is configured to facilitate a surgical procedure and enable a surgeon to reliably place discrete amounts of bone graft material into a surgical site and/or an implant. In some embodiments, the surgical injection device provides a higher level of certainty to the surgeon as to an amount of bone graft material being injected with a surgical site. In some embodiments, the surgical injection device is configured to reduce waste of the bone graft material that remains in the syringe. In some embodiments, the agent may include allograft material.

In some embodiments, the surgical injection device includes dual chambers, one for the backfill material and the other for the bone graft material. In some embodiments, the dual chamber facilitates apportioning a certain amount for one area, then using backfill material to inject it, then apportioning a second amount for a second area and using the backfill material to eject it. In some embodiments, the surgical injection device includes one-way valves configured to prevent one chamber injecting material into another chamber and directs the bone graft material into the lumen. In some embodiments, the surgical injection device is configured for mixing the bone graft material for a portion of the injection and not mixing the bone graft material for another part of the injection.

In some embodiments, the surgical injection device is utilized for filling a void of a spinal implant, such as, for example, an interbody device. In some embodiments, the surgical injection device is utilized for filling bone cavities such as gutters during a posterior lateral fusion. In some embodiments, the surgical injection device is utilized for filling an interbody space surrounding and/or adjacent to an interbody spacer. In some embodiments, the surgical injection device may include alternating layers of backfill material and bone graft material. In some embodiments, the surgical injection device may include varying textures or types of bone graft material layered various types of backfill material. In some embodiments, the type of bone graft material is selected based on the surgical procedure and injected as needed, such as, for example, chunky bone graft material, then smooth bone graft material, then backfill material. In some embodiments, the injection process is repeated as necessary, such as, for example, for filling the gutters.

In some embodiments, the backfill material may include, such as, for example, glycerol, water, saline, oil or any polysaccharide; and/or material that is flowable and biocompatible. In some embodiments, the backfill material may include, such as, for example, cement to render the surgical injection device to be a single use or disposable device. In some embodiments, the backfill or bone graft material may include, or be formed in such a way to comprise solid chunks of fine, lubricious or smooth/ball-like material that, when injected, flow similar to a liquid.

In some embodiments, the bone graft material may include, such as, for example, autograft, allograft, MASTERGRAFT®, collagen, various sized beads or geometry that could approximate a flowing mechanism when injected. In some embodiments, a viscosity of the bone graft material and a viscosity of the backfill material may be equal.

In some embodiments, the backfill material is used to bulk up the bone graft material, such as with dual syringes. For example, the bone graft material may be too strong for a certain application, such as when using BMP in the cervical spine, and so the bone graft material can be diluted using a small amount or a large amount of the backfill material. The backfill material is therefore used for driving the bone graft into the surgical site and for reducing the potency of the bone graft.

In some embodiments, the bone graft material and the backfill material are visually similar where no difference in the materials can be discerned, or the materials are made to be visually different. One benefit is to ensure that the full amount of bone graft material or backfill material is fully injected before performing the next portion of the procedure.

In some embodiments, the bone graft material that can be placed in the surgical injection device can be demineralized bone material (e.g., fibers, chips, powder, or a combination thereof). In some embodiments, the demineralized bone fibers can be elongated and have an aspect ratio of at least from about 50:1 to about at least about 1000:1. In some embodiments, the elongated demineralized bone fibers are oriented along an axis of the device, such as, along the full length of the tube of the device. The elongated bone fibers can be obtained by any one of several methods, for example, by milling or shaving the surface of an entire bone or relatively large section of bone.

In other embodiments, the length of the fibers can be at least about 3.5 cm and have an average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length be from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the bone chips can be used and they can be combined with bone fibers, where the chips to fibers ratio is about 90:10, 80:20, 70:30, 60:40, 50:50, 40:60, 30:70, 20:80 and/or 10:90, In various embodiments, a surface demineralized bone chips to fibers ratio is about 90:10, 80:20, 70:30, 60:40, 50:50, 40:60, 30:70, 20:80 and/or 10:90 that can be used in the device. In some embodiments, a surface demineralized chips to fully demineralized fibers ratio is about 90:10, 80:20, 70:30, 60:40, 50:50, 40:60, 30:70, 20:80 and/or 10:90 that can be used in the device.

In some embodiments, a viscosity of the bone graft material and a viscosity of the backfill material may be different. In some embodiments, a viscosity of the backfill material would be less than a viscosity of the bone graft material. In some embodiments, the backfill material would be as thin as possible to reduce the resistance to injection.

In some embodiments, the surgical injection device is configured to fill a void in an interbody spacer having a volume of 3 cubic centimeter (cc). In some embodiments, the surgical injection device includes a lumen having a volume of 3 cc. In some embodiments, the surgical injection device is filled with 3 cc of bone graft material and 3 cc of backfill material such that the backfill material evacuates the entire 3 cc of bone graft material into the 3 cc void of the interbody spacer. The volumes stated herein are for reference only, and any volume that is appropriate in relation to the size of the devices being used and filled can be applied.

In some embodiments, the surgical injection device includes a dual syringe device including one syringe to dispense a specific amount of bone graft material and a second syringe configured to dispense a specific amount of backfill material. In some embodiments, the bone graft material syringe is activated to fill a void. In some embodiments, a filling tube is attached with the dual syringe device. In some embodiments, the bone graft material is configured to fill the filling tube. In some embodiments, a positive pressure is applied to the backfill material syringe to resist and/or prevent bone graft material from entering into the backfill material syringe. In some embodiments, the dual syringe device includes a one-way valve to resist and/or prevent one material from entering into the syringe of the other material.

In some embodiments, the backfill material syringe is activated to evacuate the bone graft material from the filling tube into the implant. In some embodiments, the bone graft material syringe can be activated again to fill a second void. In some embodiments, the bone graft material syringe and the backfill material syringe can be simultaneously activated. In one embodiment, the backfill syringe is filled with radiopaque material such that at certain intervals, the surgeon can see how much bone graft material has been injected. In one embodiment, the surgeon injects 0.1 cc of the radiopaque marker material in between each 1 cc apportioning of bone graft material such that as the device fills, each radiopaque marker layer indicates the amount of bone graft material that has entered the interbody device. In some embodiments, the surgical injection device may include more than two syringes to provide various bone graft materials having different material properties. In some embodiments, the system may comprise 3 or more syringes.

In some embodiments, the surgical injection device includes a tube prepackaged with bone graft material. In some embodiments, the tube is configured for connection with a pressure applying device, such as, for example, a syringe to evacuate the bone graft material from the tube. In some embodiments, the bone graft material is enclosed within the tube by a cap at one or both ends. In some embodiments, the tube includes a stopper. In some embodiments, the tube is attachable with a luer lock connector. In some embodiments, the tube includes an end configured for connection with an irrigation instrument.

In some embodiments, a method for utilizing the prepackaged tube includes the step of removing the caps from one or both ends. In some embodiments, a method for utilizing the prepackaged tube includes attaching the tube to an implant.

In some embodiments, the surgical injection device includes plugs configured to be internal or substantially internal within the tube. In some embodiments, the plugs are configured for implantation with the bone graft material, eliminating the need to remove the plugs prior to applying the bone graft material.

In some embodiments, one or all of the components of the surgical system are disposable, peel-pack, pre-packed sterile devices that can be used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise, or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-7, there are illustrated components of a surgical system 10 including a surgical injection device 12.

The components of surgical system 10 can be fabricated from biologically acceptable materials suitable for medical applications, including metals, synthetic polymers, ceramics and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), calcium sulfate, or other resorbable polymers such as polylactide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 including surgical injection device 12 can be employed, for example, with percutaneous surgical implantation, minimally invasive surgery, mini-open and open surgical techniques to prepare a surgical site including tissue in connection with a surgical procedure, introduction of surgical instrumentation and/or delivery and introduction of one or more biomaterials and/or an implant, such as, for example, spinal implants, rods, fasteners, connectors, plates, an intervertebral implant, interbody devices and arthroplasty devices at a surgical site within a body of a patient, for example, a section of a spine. In some embodiments, surgical system 10 may be employed with surgical procedures, such as, for example, decompression, corpectomy and discectomy, which can include fusion and/or fixation treatments that employ implants.

Surgical injection device 12 includes a plurality of tubular elements, such as, for example, a syringe barrel 14 and tubing 16 that define a passageway P. An evacuator, such as, for example, a flowable backfill material 32 is engageable with a selected volume V of an agent, such as, for example, bone graft material 30 within passageway P to entirely expel selected volume V of bone graft 30 from passageway P to a void of a selected site, as described herein. In some embodiments, surgical injection device 12 can include a single tubular element, or a plurality of tubular elements that are integrally connected or monolithically formed.

In some embodiments, bone graft 30 is configured for disposal into barrel 14 in a dry state. In some embodiments, surgical injection device 12 is configured for withdrawing blood or liquid via suction or vacuum from a selected site (e.g., disc space) to hydrate dry bone graft 30. In some embodiments, after bone graft 30 is hydrated, it is injected into the selected site.

In some embodiments, bone graft 30 can be withdrawn from a selected site. In some embodiments, when bone graft 30 is injected into the wrong site, or if bone graft 30 has been injected into a site due to an emergency, surgical injection device 12 is configured to withdraw bone graft 30 from the site via suction or vacuum.

Barrel 14 extends between a proximal end 18 and a distal end 20. End 18 defines an opening 22 configured for disposal of an actuator, such as, for example, a plunger 42, as described herein. End 20 defines an opening 24 and is configured for connection with tubing 16, as described herein. In some embodiments, end 20 includes a tip having a taper, nozzle, valve and/or luer lock connection for connecting with tubing 16. In some embodiments, end 20 includes a pressure fit, friction fit or threaded connection for connecting with tubing 16. In some embodiments, end 20 is integrally connected or monolithically formed with tubing 16.

Barrel 14 defines a longitudinal axis X1, as shown in FIG. 5. In some embodiments, barrel 14 may have cross section configurations, such as, for example, oval, cylindrical, triangular, square, polygonal, irregular, uniform, non-uniform, offset, staggered, undulating, arcuate, variable and/or tapered. In some embodiments, a wall of barrel 14 can be flexible, elastic, semi-rigid or rigid.

Barrel 14 includes a surface 26. Surface 26 defines a cavity, such as, for example, a passageway 28. Passageway 28 defines a portion of passageway P, as described herein. Passageway 28 extends along axis X1 between ends 18, 20. Passageway 28 is configured for disposal of bone graft 30 and backfill 32, as described herein. In some embodiments, passageway 28 may have cross section configurations, such as, for example, oval, cylindrical, triangular, square, polygonal, irregular, uniform, non-uniform, offset, staggered, undulating, arcuate, variable and/or tapered.

In some embodiments, barrel 14 includes a visual indicia, such as, gradations on an outer surface configured to provide a visual indication of the amount of material injected. In some embodiments, a portion or the entire barrel 14 is transparent to provide a visual indication of the amount of material that remains in barrel 14.

Tubing 16 is configured for attachment with a tip of barrel 14 adjacent opening 24. Tubing 16 extends between an end 60 and an end 62. End 60 includes a surface 64. Surface 64 is connected with the tip of barrel 14 in various configurations, such as, for example, luer lock connection, friction fit, pressure fit, locking protrusion/recess, locking keyway and/or adhesive. End 62 is configured for disposal adjacent a void of the selected site, as described herein, as bone graft 30 is entirely expelled from passageway P.

Tubing 16 includes a surface 66 that defines a cavity, such as, for example, a passageway 68. Tubing 16 is attached with the tip of barrel 14 adjacent opening 24 to connect passageway 28 with passageway 68 to form passageway P. Passageway 68 is configured for passage of bone graft 30 and backfill 32 such that selected volume V of bone graft 30 is entirely expelled from passageway P to the void of the selected site, as described herein. In some embodiments, passageway 68 may have cross section configurations, such as, for example, oval, cylindrical, triangular, square, polygonal, irregular, uniform, non-uniform, offset, staggered, undulating, arcuate, variable and/or tapered. It will be understood that the tubing 16 can be any length depending on the surgical procedure.

In some embodiments, tubing 16 includes a visual indicia, such as, gradations on an outer surface configured to provide a visual indication of the amount of material injected. In some embodiments, a portion or the entire tubing 16 is transparent to provide a visual indication of the amount of material that remains in tubing 16.

In some embodiments, radiopaque markers are positioned on the tip and tubing 16 is made from a radiolucent material. In some embodiments, the tube comprises a steering member that allows the tip to be steerable so that the angle of surface 64 can be changed and the magnitude. In some embodiments, the steerable tip utilizes similar technology as a steerable catheter (e.g., multiple lumens, with one being used for a wire to pull the tip). In some embodiments, end of tubing 16 can be closed or have an opening and the surface of tubing can have one or a plurality of openings or fenestrations for dispensing graft material and/or fluid. In some embodiments, these openings can be disposed at an angle and/or orientation for dispensing the graft material and/or fluid to the desired site or sites. In some embodiments, the plurality of fenestrations can also be oriented along the tube to give a line of dispensing, rather than a point of dispensing. In some embodiments, the plurality of fenestrations can be approximated by a single long opening.

In some embodiments, the surface of tubing 16 can have one or a plurality of openings for dispensing graft material and/or fluid and the device can include a handle for orienting the openings. The handle can be rotated, translated or pivoted to the proper orientation for delivery of the graft material and/or fluid.

Selected volume V of bone graft 30 is configured to flow through passageway P into a selected site. In some embodiments, bone graft 30 includes a viscosity configured to reduce resistance with surface 26 and facilitate flow within passageway P. In some embodiments, bone graft 30 includes a lubricating material. In some embodiments, bone graft 30 may include, such as, for example, bone material including autograft, allograft, xenograft, MASTERGRAFT®, collagen or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, TCP, HA-TCP, calcium sulfate, or other resorbable polymers such as polylactide, polyglycolide, polytyrosine carbonate, polycaprolactone and their combinations.

In some embodiments, bone graft 30 comprises demineralized bone material. The demineralized bone material can be comprise demineralized bone, powder, chips, triangular prisms, spheres, cubes, cylinders, shards, fibers or other shapes having irregular or random geometries. These can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized.

In some embodiments, bone graft 30 comprises at least one growth factor. These growth factors include osteoinductive agents (e.g., agents that cause new bone growth in an area where there was none) and/or osteoconductive agents (e.g., agents that cause in growth of cells into and/or through the allograft). Osteoinductive agents can be polypeptides or polynucleotides compositions. Polynucleotide compositions of the osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art, (See, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Embodiments of variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

In some embodiments, isolated osteoinductive agents that are included in bone graft 30 are sterile. In a non-limiting method, sterility is readily accomplished for example by filtration through sterile filtration membranes (e.g., 0.2 micron membranes or filters). In one embodiment, the isolated osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents include one or more members of the family of Transforming Growth Factor-beta genes ("TGF-betas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same.

In another embodiment, isolated osteoinductive agents include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents include, but are not limited to, the following CDMPs and LMPs: CDMP-1 polynucleotides and polypeptides corresponding to GenBank Accession Numbers NM_00557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents include one or more members of any one of the families of Bone Morphogenetic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), TP508 (an angiogenic tissue repair peptide), as well as mixtures or combinations thereof.

In another embodiment, the one or more isolated osteoinductive agents useful in bone graft 30 are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and or combination thereof; Osteoprotegerin; TGF-beta-1, TGF-beta-2, TGF-beta-3, or any combination thereof; or any combination of one or more members of these groups.

In some embodiments, a statin may be used as the growth factor. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

The growth factor may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the growth factor may comprise sterile and/or preservative free material.

These above inactive ingredients may have multi-functional purposes including the carrying, stabilizing and controlling the release of the growth factor and/or other therapeutic agent(s). The sustained release process, for example, may be by a solution-diffusion mechanism or it may be governed by an erosion-sustained process.

In some embodiments, the growth factor is supplied in an aqueous buffered solution. Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM.

In some embodiments, the BMP-2 is provided in a vehicle (including a buffer) containing sucrose, glycine, L-glutamic acid, sodium chloride, and/or polysorbate 80.

In some embodiments, bone graft 30 comprises therapeutic agents. Exemplary therapeutic agents include but are not limited to IL-1 inhibitors, such Kinerete (anakinra), which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dilhiocarbamate, and other compounds, such as, for example, sulfasalazine.

Examples of therapeutic agents suitable for use also include, but are not limited to an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In some embodiments, bone graft 30 includes at least one antimicrobial. Antimicrobial includes, for example, antibiotics, antifungal, antiviral agents or the like. Antimicrobial agents to treat infection include by way of example and not limitation, antiseptic agents, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Some exemplary antimicrobial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; barribermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natamycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Backfill 32 is configured to flow through passageway P to expel selected volume V of bone graft 30 into a selected site. In some embodiments, a viscosity of backfill 32 facilitates driving bone graft 30 from passageway 28, through passageway 68 and into a selected site. In some embodiments, the viscosity of backfill 32 is lower than the viscosity of bone graft 30 to facilitate movement of bone graft 30 through passageway P. In some embodiments, the viscosity of bone graft 30 is equal to the viscosity of backfill 32. In some embodiments, the evacuator may include a solid, liquid or gaseous substance, and/or include a mechanical element such as a gasket, disc, stopper or plunger.

In some embodiments, backfill 32 may include, such as, for example, sterile water, glycerol, saline, oil or any polysaccharide; and/or material that is flowable and biocompatible, such as, for example, blood, or blood components including plasma, platelet-rich plasma, buffy coat. In some embodiments, backfill 32 may include, such as, for example, cement to render surgical injection device 12 to be a single use device and/or disposable. In some embodiments, backfill 32 may include, such as, for example, solid chunks of material that, when injected, flow similar to a liquid.

Plunger 42 actuates movement of backfill 32 and bone graft 30 within passageway P. Plunger 42 extends between an end 44 and an end 46. End 44 includes a handle 48 configured for manipulation to translate plunger 42 relative to the wall of barrel 14 within passageway 28. End 46 includes a plunger seal 50 that slidably engages the wall of barrel 14 such that plunger 42 is movably disposed with opening 22. Plunger seal 50 is configured to resist and/or prevent backfill 32 and/or bone graft 30 from exiting opening 22.

Figure 7:
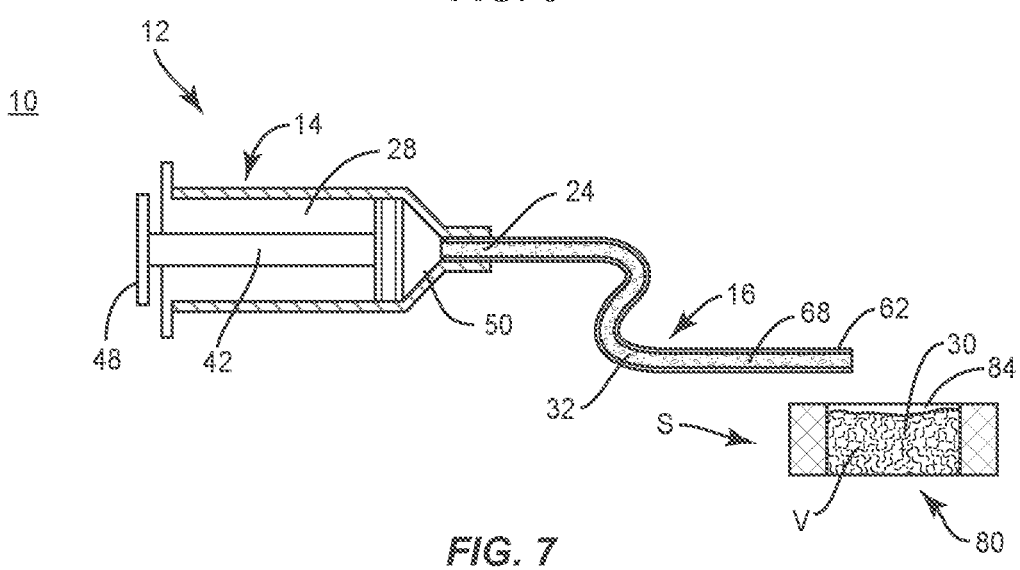
FIG. 7 is a cross section view of the components shown in FIG. 5.

Plunger seal 50 is configured to translate within passageway 28 and contact backfill 32. Plunger 42 translates relative to barrel 14 between an initial orientation, as shown in FIG. 5, and a fully or entirely expelled orientation, as shown in FIG. 7. In the initial orientation, plunger 42 is disposed adjacent backfill 32. Plunger 42 translates, in the direction shown by arrow A in FIG. 5, such that plunger seal 50 applies a force to backfill 32. The force applied by plunger seal 50 causes backfill 32 to compress bone graft 30. Compression of bone graft 30 causes bone graft 30 to flow from passageway 28 through opening 24. Further translation of plunger 42 causes backfill 32 to force bone graft 30 into passageway 68, as shown by in FIG. 6. Translation of plunger 42 to the entirely expelled orientation causes backfill 32 to flow into passageway 68 forcing bone graft 30 through passageway 68 to entirely expel selected volume V of bone graft 30 into a selected site, for example, as shown in FIG. 7.

In some embodiments, bone graft 30 is disposed in a series configuration with backfill 32 within passageway P such that selected volume V of bone graft 30 can be entirely expelled by backfill 32. In some embodiments, entirely expelling the entire selective volume V of bone graft 30 includes particulate and/or residue of bone graft 30 remaining on the surfaces that define passageway P. In some embodiments, bone graft 30 and backfill 32 are disposed in layers, such as, for example, alternating layers of bone graft 30 and backfill 32 within passageway 28. In some embodiments, an alternating layer configuration of bone graft 30 and backfill 32 is configured to facilitate selective filling of the selected site S with bone graft 30 and backfill 32. In some embodiments, the surgeon adds 2 cc of bone graft 30 at the base of at least one bone fastener, and adds 1 cc of backfill 32 to facilitate confirmation of full injection of bone graft 30. In some embodiments, barrel 14 comprises multiple layers of 2 cc of bone graft 30 interspersed with 1 cc layers of backfill 32.

In some embodiments, the selected site includes, for example, an interbody implant 80. In some embodiments, interbody implant 80 includes a surface 82. Surface 82 defines a void 84. Void 84 is configured to receive the selected volume V of bone graft 30. In some embodiments, the cross-section geometry of interbody implant 80 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape.

In assembly, operation and use, surgical system 10, similar to the systems and methods described herein, includes surgical injection device 12 and is employed to treat an affected section of a patient body, such as, for example, vertebrae with a spinal implant, such as, for example, interbody implant 80. Surgical system 10 may be used with surgical methods or techniques including open surgery, mini-open surgery, minimally invasive surgery and percutaneous surgical implantation, whereby vertebrae are accessed through a mini-incision, or sleeve that provides a protected passageway to a surgical site. Once access to the surgical site is obtained, a surgical treatment, similar to those described herein and for example, a spinal stabilization procedure can be performed for treating a spine disorder. In some embodiments, a diseased and/or damaged portion of the vertebrae can be removed and an intervertebral space is prepared for interbody implant 80.

The components of surgical system 10 including surgical injection device 12 are employed to augment the surgical treatment. In some embodiments, surgical injection device 12 can introduce or deliver a selected volume V of bone graft 30 into interbody implant 80 prior, during and/or subsequent to disposal of interbody implant 80 with vertebrae at selected surgical site S. In some embodiments, surgical injection device 12 can inject selected volume V of bone graft 30 into interbody implant 80 in vivo. In some embodiments, surgical injection device 12 can inject selected volume V of bone graft 30 directly adjacent or into the vertebrae at selected surgical site S.

Surgical injection device 12 is provided with a selected volume V, such as, for example, 3 cc of bone graft 30, as shown in FIG. 5. Surgical injection device 12 is provided with a volume of backfill 32, such as, for example, 3 cc of backfill 32. End 62 of tubing 16 is disposed adjacent void 84 of interbody implant 80. In some embodiments, void 84 is configured to receive 3 cc of bone graft 30.

From the initial orientation, a force is applied to plunger 42 and/or plunger 42 is manipulated such that plunger 42 translates in the direction shown by arrow A in FIG. 5. Plunger seal 50 applies a force to backfill 32 to compress bone graft 30 adjacent opening 24, as described herein. Continued manipulation of plunger 42 causes bone graft 30 to flow from passageway 28 through opening 24 such that backfill 32 forces bone graft 30 into passageway 68, as shown by in FIG. 6. As plunger 42 is further manipulated, backfill 32 flows into passageway 68 forcing bone graft 30 through passageway 68 to entirely expel selected volume V of bone graft 30 from passageway P into void 84 at selected site S, as shown in FIG. 7.

In some embodiments, surgical system 10 comprises a kit including a plurality of interbody devices, connectors, plates, bone fasteners and/or fixation elements, which may be employed with a single vertebral level or a plurality of vertebral levels. Upon completion of the procedure, the surgical instruments, assemblies and non-implanted components of surgical system 10 are removed and the incision is closed. The components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10.

In some embodiments, the components of surgical system 10 contain radiomarkers and/or radioopacity enhancing agents. In some embodiments, the radiomarkers and/or radioopacity enhancing agents enable the surgeon the ability to visualize (e.g., via c-arm radiography) the delivery of bone graft 30 to the site and assess the quality of fill at the intended delivery site. In some embodiments, the radiomarkers include, but are not limited to, barium, calcium phosphate, bismuth, iodine, tantalum, tungsten, and/or metal beads or particles.

Figure 8:
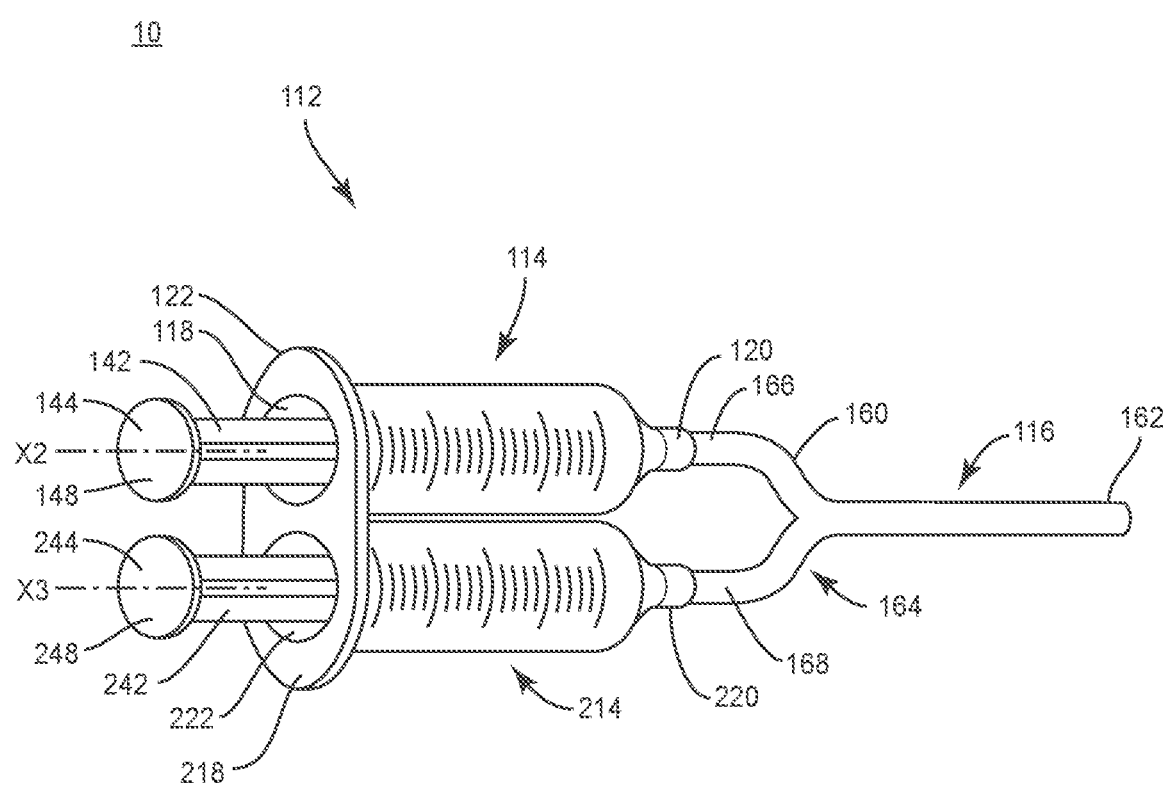
FIG. 8 is a perspective view of components of one embodiment of a surgical system in accordance with the principles of the present disclosure.

In one embodiment, as shown in FIGS. 8-11, surgical system 10, similar to the systems and methods described above with regard to FIGS. 1-7, includes a surgical injection device 112, similar to surgical injection device 12 described herein. Surgical injection device 112 includes a syringe barrel 114, a syringe barrel 214 and tubing 116. Barrel 114 extends between an end 118 and an end 120. End 118 defines an opening 122 configured for disposal of an actuator, such as, for example, a plunger 142, similar to plunger 42 described herein. End 120 defines an opening 124 and a tip configured for connection with tubing 116, similar to that described herein. Barrel 114 defines a longitudinal axis X2, as shown in FIG. 8.

Barrel 114 includes a surface 126. Surface 126 defines a passageway 128. Passageway 128 defines a portion of a fluid passageway P1, similar to that described herein. Passageway 128 extends along axis X2 between ends 118, 120. Passageway 128 is configured for disposal of a selected volume V1 of bone graft material 130, similar to that described herein.

Plunger 142 is movably disposed with opening 122. Plunger 142 is configured to actuate movement of bone graft 130 within passageway 128. Plunger 142 includes a plunger seal 150 that slidably engages the wall of barrel 114 such that plunger 142 is movably disposed with opening 122. Plunger seal 150 is configured to resist and/or prevent bone graft 130 from exiting opening 122.

Figure 9:
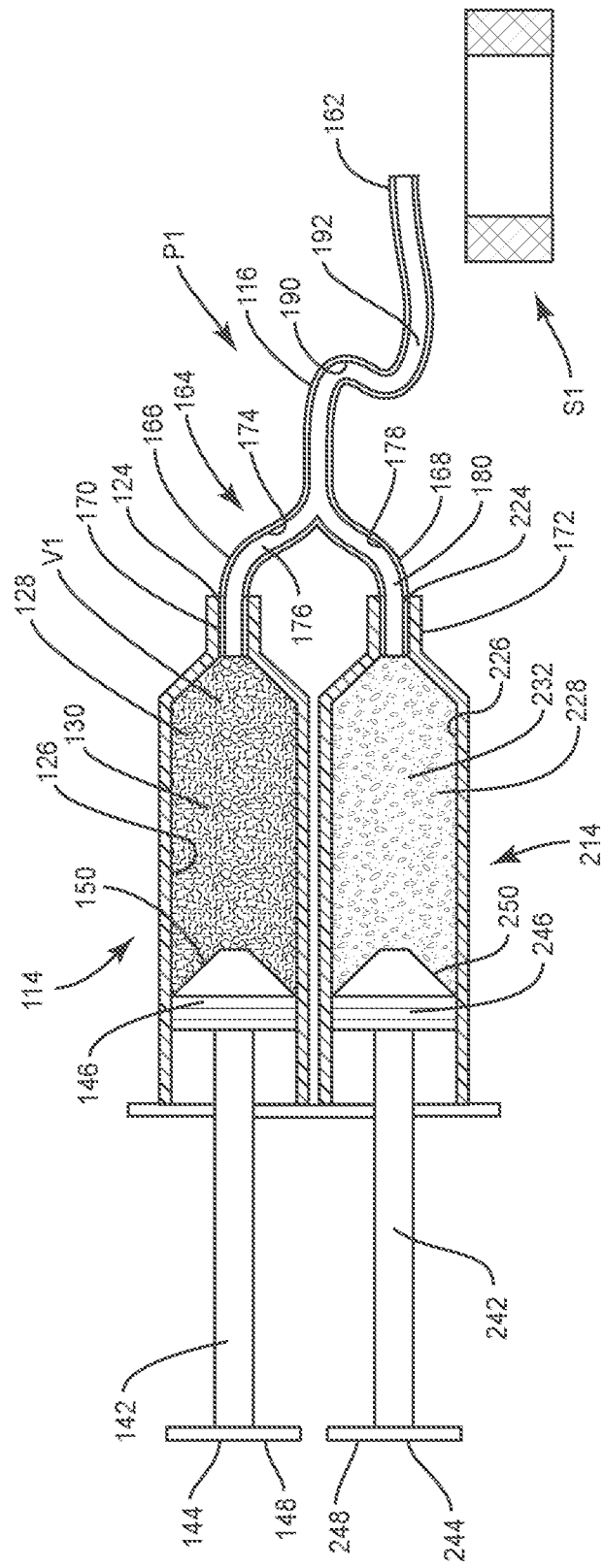
FIG. 9 is a cross section view of components of one embodiment of a surgical system in accordance with the principles of the present disclosure.
Figure 10:
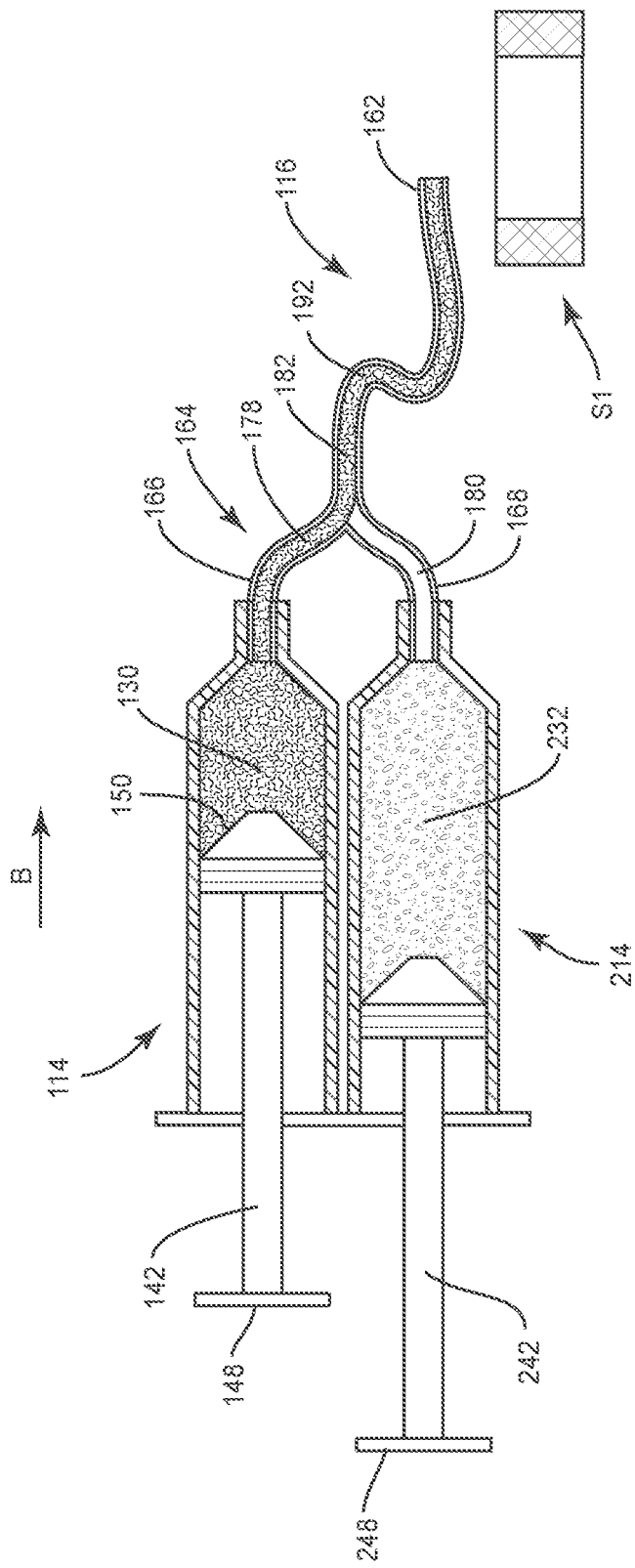
FIG. 10 is a cross section view of the components shown in FIG. 9.

Plunger seal 150 is configured to translate within passageway 128 and contact bone graft 130. Plunger 142 is configured to translate relative to barrel 114 between an initial orientation, as shown in FIG. 9, and a dispensing orientation, as shown in FIG. 10. In the initial orientation, plunger 142 is disposed adjacent bone graft 130. Plunger 142 is configured for translation, in the direction shown by arrow B in FIG. 10, such that plunger seal 150 applies a force to bone graft 130. The force applied by plunger seal 150 causes bone graft 130 to flow from passageway 128 through opening 124 into tubing 116, similar to that described herein.

Barrel 214 extends between an end 218 and an end 220. End 218 defines an opening 222 configured for disposal of a plunger 242, similar to plunger 42 described herein. End 220 defines an opening 224 and a tip configured for connection with tubing 116, similar to that described herein. Barrel 214 defines a longitudinal axis X3, as shown in FIG. 8. In some embodiments, axis X3 is disposed parallel to axis X2. In some embodiments, axis X3 may be disposed at alternate orientations relative to axis X2, such as, for example, transverse and/or other angular orientations, such as, acute or obtuse.

Barrel 214 includes a surface 226. Surface 226 defines a passageway 228. Passageway 228 defines a portion of fluid passageway P1. Passageway 228 extends along axis X3 between ends 218, 220. Passageway 228 is configured for disposal of backfill material 232, similar to that described herein.

Plunger 242 is movably disposed with opening 222. Plunger 242 is configured to actuate movement of bone fill 232 within passageway 228. Plunger 242 includes a plunger seal 250 that slidably engages the wall of barrel 214 such that plunger 242 is movably disposed with opening 222. Plunger seal 250 is configured to resist and/or prevent backfill 232 from exiting opening 222.

Figure 11:
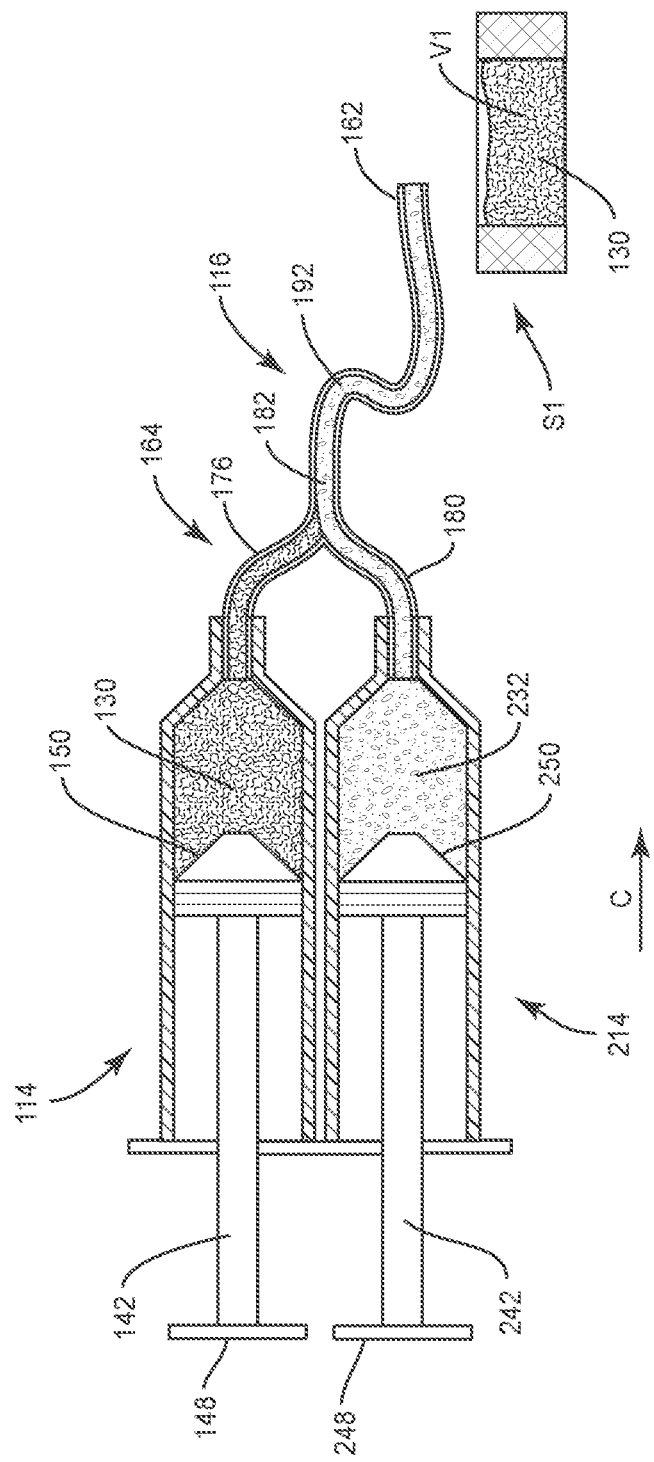
FIG. 11 is a cross section view of the components shown in FIG. 9.
Figure 16:
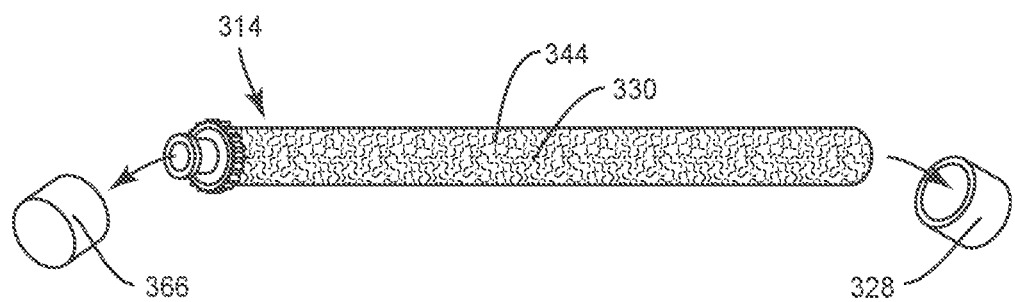
FIG. 16 is a perspective view, with parts separated, of components of one embodiment of a surgical system in accordance with the principles of the present disclosure.
Figure 17:
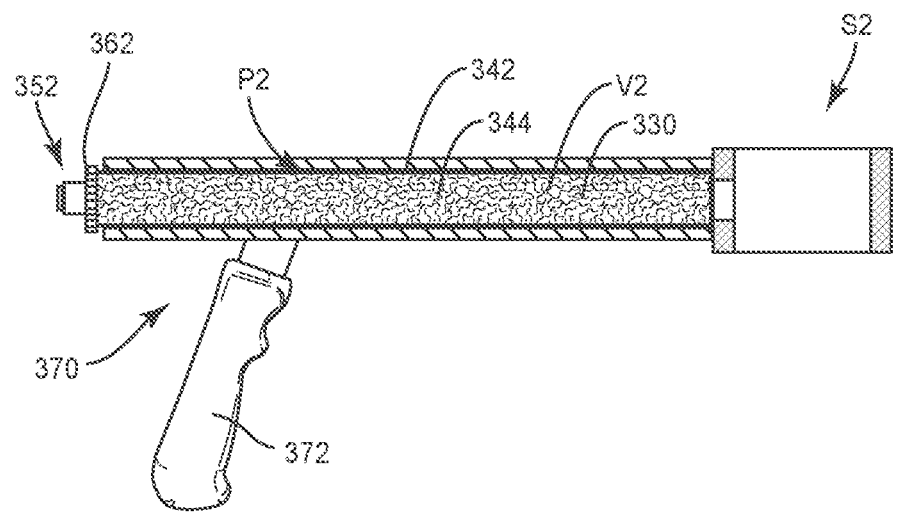
FIG. 17 is a cross section view of components of one embodiment of a surgical system in accordance with the principles of the present disclosure.

Plunger seal 250 is configured to translate within passageway 228 and contact backfill 232. Plunger 242 is configured to translate relative to barrel 214 between an initial orientation, as shown in FIG. 9 and a fully or entirely expelled orientation, as shown in FIG. 11. In the initial orientation, plunger 242 is disposed adjacent backfill 232. Plunger 242 is configured for translation, in the direction shown by arrow C in FIG. 11, such that plunger seal 250 applies a force to backfill 232. The force applied by plunger seal 250 causes backfill 232 to flow from passageway 228 through opening 224. Further translation of plunger 242 causes backfill 232 to flow into tubing 116, similar to that described herein.

Tubing 116 extends between an end 160 and an end 162. Tubing 116 is configured for connection with openings 124, 224, as described herein. In some embodiments, end 160 includes a bifurcated extension 164 having a part 166 and a part 168. Part 166 includes a surface 170. In some embodiments, surface 170 is connected with the tip of barrel 114, similar to that described herein. Part 166 includes a surface 174 that defines a passageway 176. Part 166 is connected with barrel 114 to orient passageway 176 in communication with passageway 128.

Part 168 includes a surface 172. In some embodiments, surface 172 is connected with the tip of barrel 214, similar to that described herein. Part 168 includes a surface 178 that defines a passageway 180. Part 168 is connected with barrel 214 to orient passageway 180 in communication with passageway 228. Passageways 176, 180 merge into a passageway 192. In some embodiments, passageways 176, 180 merge at a juncture, such as, for example, a mixing chamber 182, which may be employed to selectively combine one or more agents and backfill, as described herein.

Tubing 116 includes a surface 190. Surface 190 defines passageway 192. Passageway 192 is in communication with passageways 176, 180 to form a portion of passageway P1. Passageway 192 is configured for passage of selected volume V of bone graft 130 and backfill 232. End 162 is configured for engagement with selected site S1 to direct the flow of selected volume V1 of bone graft 130 into selected site S1, similar to that described herein.

Backfill 232 is configured to force bone graft 130 through chamber 182, as shown by in FIG. 11. Translation of plunger 242 into the fully or entirely expelled orientation causes backfill 232 to flow into chamber 182 forcing bone graft 130 through passageway 192 to entirely expel selected volume V1 of bone graft 130 into selected site S1, as shown in FIG. 11 and similar to that described herein.

In some embodiments, barrel 114 is disposed in a side by side configuration with barrel 214. In this configuration, selected volume V of bone graft 130 is injected into tubing 116 prior to injection of backfill 232 into tubing 116. In some embodiments, bone graft 130 and backfill 232 are injected into tubing 116 in stages to form layers, such as, for example, alternating layers of bone graft 130 and backfill 232 within selected site S1. In some embodiments, barrel 114 includes a one way valve disposed adjacent end 120 that is configured to resist and/or prevent backflow of bone graft 130 into passageway 128. In some embodiments, barrel 214 includes a one way valve disposed adjacent end 220 that is configured to resist and/or prevent backflow of backfill 232 into passageway 228.

In some embodiments, barrel 114 and barrel 214 are the same size. In some embodiments, barrel 114 and barrel 214 are different sizes depending on the desired number of applications of bone graft 130, volume of lumen and selected site S1.

Figure 18:
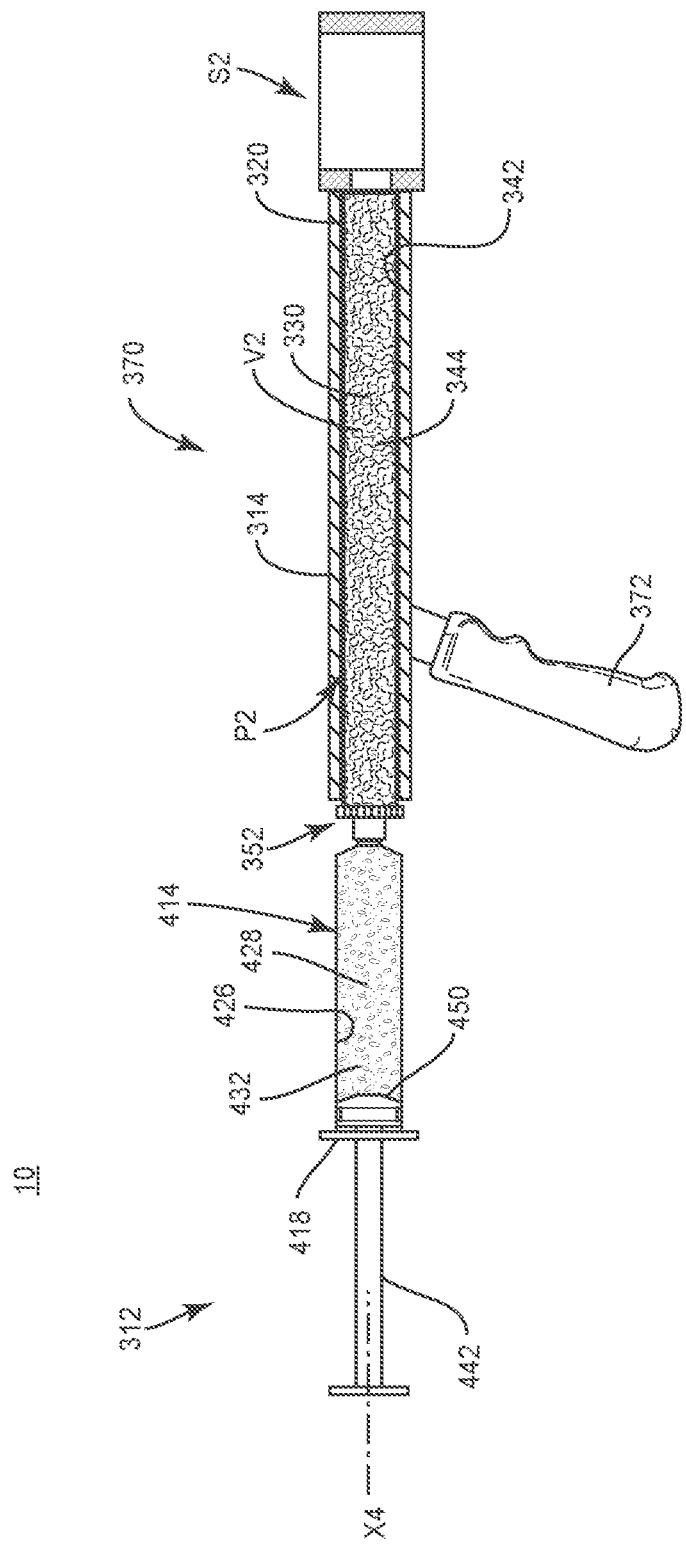
FIG. 18 is a cross section of components of one embodiment of a surgical system in accordance with the principles of the present disclosure.
Figure 19:
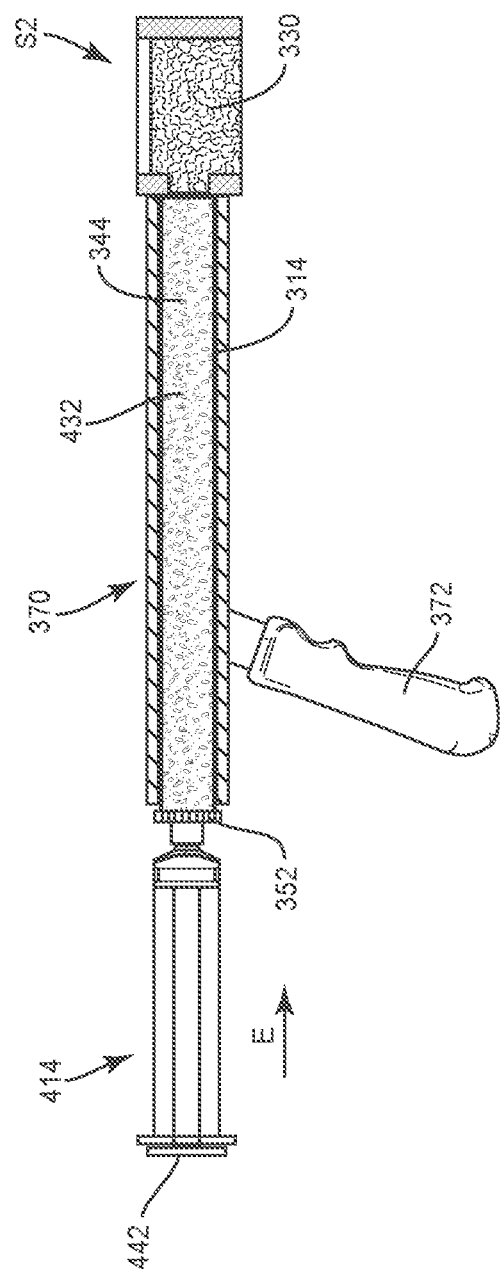
FIG. 19 is a cross section view of the components shown in FIG. 18.

In one embodiment, as shown in FIGS. 12-19, surgical system 10, similar to the systems and methods described herein, includes a surgical injection device 312, similar to the surgical injection devices described herein. Surgical injection device 312 includes a tubular element, such as, for example, a tube 314 and a syringe barrel 414, as described herein. Tube 314 extends between an end 318 and an end 320. End 318 includes a luer lock connection 352, as shown in FIG. 15. In some embodiments, luer lock 352 is configured to facilitate attachment of barrel 414 with tube 314, as described herein. In some embodiments, end 318 includes a flange 362. Flange 362 is configured for engagement with barrel 414 to resist and/or prevent separation of barrel from tube 314, as shown in FIG. 18. End 320 defines an opening 324 configured for connection with a selected site S2. Tube 314 defines a longitudinal axis X4, as shown in FIG. 18.

In some embodiments, end 318 is configured for connection with a tip 325, as shown in FIG. 15. In some embodiments, tip 325 is configured to facilitate connection with an irrigation instrument. In some embodiments, tip 325 is configured to facilitate connection with an irrigation instrument. In some embodiments, tube 314 is prepackaged with a selected volume V2 of bone graft 330, similar to that described herein. In some embodiments, tube 314 includes a cap 326 engageable with end 318 to prevent bone graft 330 from exiting opening 322, as shown in FIG. 13. In some embodiments, tube 314 includes a cap 328 engageable with end 320 to prevent bone graft from exiting opening 324.

Tube 314 includes a surface 342. Surface 342 defines a passageway 344. Passageway 344 defines a portion of a fluid passageway P2, similar to that described herein. Passageway 344 extends along axis X4 between ends 318, 320. Passageway 344 is configured for disposal of a selected volume V2 of bone graft material 330, similar to that described herein. Selected volume V2 of bone graft 330 is configured to flow through passageway P2 into selected site S2.

Barrel 414 includes a surface 426. Surface 426 defines passageway 428. Passageway 428 defines a portion of a fluid passageway P2, as described herein. Passageway 428 extends along axis X4. Passageway 428 is configured for disposal of backfill 432 configured for actuation by a plunger 442, as described herein.

Plunger 442 includes a plunger seal 450. Plunger seal 450 is configured to apply a force to backfill 432 causing bone graft 330 to be expelled from tubing 314, as described herein. Plunger 442 is configured for translation relative to the wall of barrel 414 within passageway 428. In some embodiments, plunger 442 is configured to translate relative to barrel 414, in the direction shown by arrow E in FIG. 19, to engage backfill 432 to entirely expel selected volume V2 of bone graft 330 from passageway P2 into selected site S2, similar to that described herein.

In some embodiments, tube 314 includes a visual indicia, such as, gradations on an outer surface configured to provide a visual indication of the amount of material injected. In some embodiments, a portion or the entire tube 314 is transparent to provide a visual indication of the amount of material that remains in tube 314.

In some embodiments, a surgical instrument, such as, for example, an inserter 370 including a cannula for disposal of surgical injection device 312 is employed to facilitate connection with selected site S2, as shown in FIG. 18. Inserter 370 is configured to facilitate introduction and/or delivery of the components of surgical system 10 to a surgical site, as described herein, and/or engage selected site S2. In some embodiments, inserter 370 may include one or more needles, trocars, sheaths and/or minimally invasive instruments. In some embodiments, inserter 370 may include a cutting surface that can be extended and retracted to cut and/or sever tissue and/or components of surgical system 10. In some embodiments, inserter 370 may be guided via imaging guidance, as described herein. In some embodiments, inserter 370 includes a handle 372 configured to facilitate manipulation and positioning of surgical injection device 312.

In one embodiment, as shown in FIGS. 20-23, surgical system 10, similar to the systems and methods described herein, includes a surgical injection device 512, similar to the surgical injection devices described herein. Surgical injection device 512 includes a tubular element, such as, for example, a tube 514 and a plunger 552, similar to that described herein. Tube 514 extends between an end 518 and an end 520.

Figure 20:
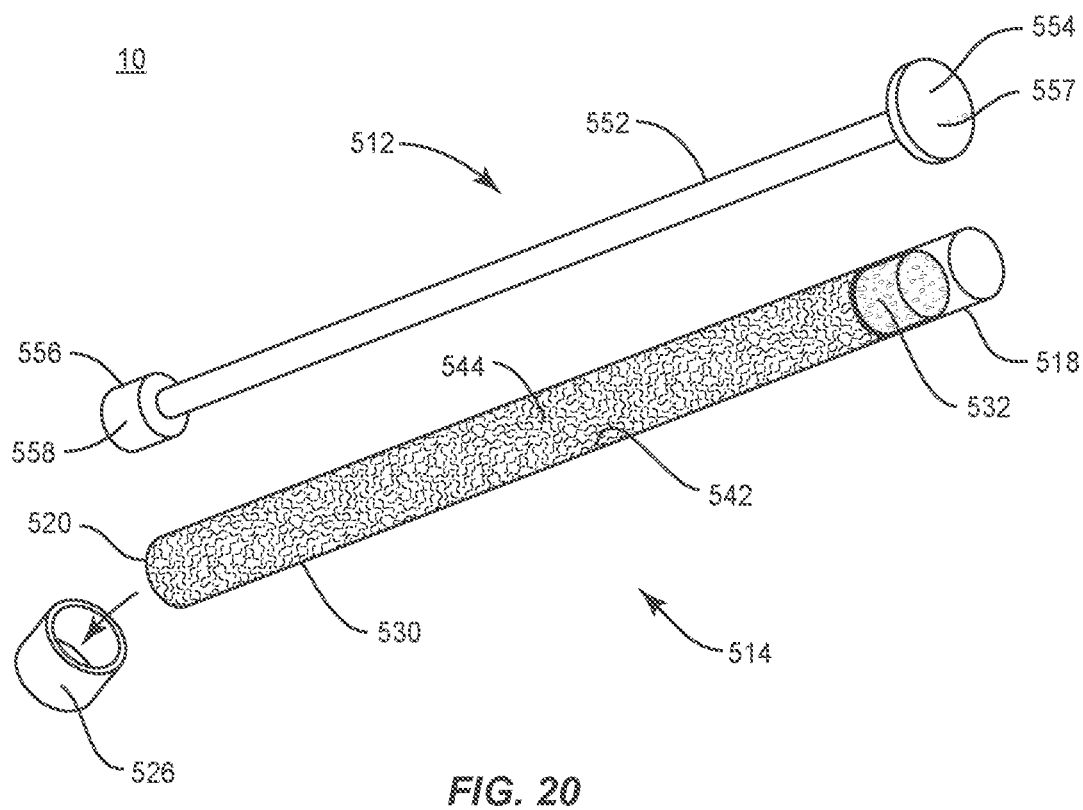
FIG. 20 is a perspective view of components of one embodiment of a surgical system in accordance with the principles of the present disclosure, with parts separated.

Tube 514 includes a surface 542. Surface 542 defines a passageway 544. Passageway 544 defines a portion of a fluid passageway P3, similar to that described herein. Passageway 544 extends along axis X5 between ends 518, 520. Passageway 544 is configured for disposal of a selected volume V3 of bone graft material 530, similar to that described herein. Selected volume V3 of bone graft 530 is configured to flow through passageway P3 into selected site S3. In some embodiments, tube 514 is prepackaged with a selected volume V3 of bone graft 530, similar to that described herein. In some embodiments, tube 514 includes a cap 526 engageable with end 520 to prevent bone graft 530 from exiting tube 514, as shown in FIG. 20.

In some embodiments, tube 514 includes an evacuator, such as, for example, a stopper 532 that is disposed adjacent end 518. In some embodiments, stopper 532 includes a biocompatible material, similar to that described herein, and is configured for disposal with selected site S3. In some embodiments, stopper 532 is configured to facilitate expelling the entire selected volume V3 of bone graft 530 from tube 514, similar to that described herein.

Plunger 552 is engageable with tube 514 and translatable relative to a wall of tube 514 to entirely expel bone graft 530 from passageway P3, as described herein. Plunger 552 extends between an end 554 and an end 556. End 554 includes a handle 557 configured for manipulation to translate plunger 552 within passageway 544. Plunger 552 includes a plunger seal 558 configured to apply a force to stopper 532 and/or bone graft 530, similar to that described herein. In some embodiments, plunger 552 is configured to translate relative to tube 514, as shown in FIGS. 22 and 23, such that plunger seal 558 engages stopper 523, which entirely expels selected volume V3 of bone graft 530 from passageway P3 into selected site S3, for example, a void of an interbody implant, similar to that described herein.

In some embodiments, tube 514 includes a visual indicia, such as, gradations on an outer surface configured to provide a visual indication of the amount of material injected. In some embodiments, a portion or the entire tube 514 is transparent to provide a visual indication of the amount of material that remains in tube 514.

Figure 21:
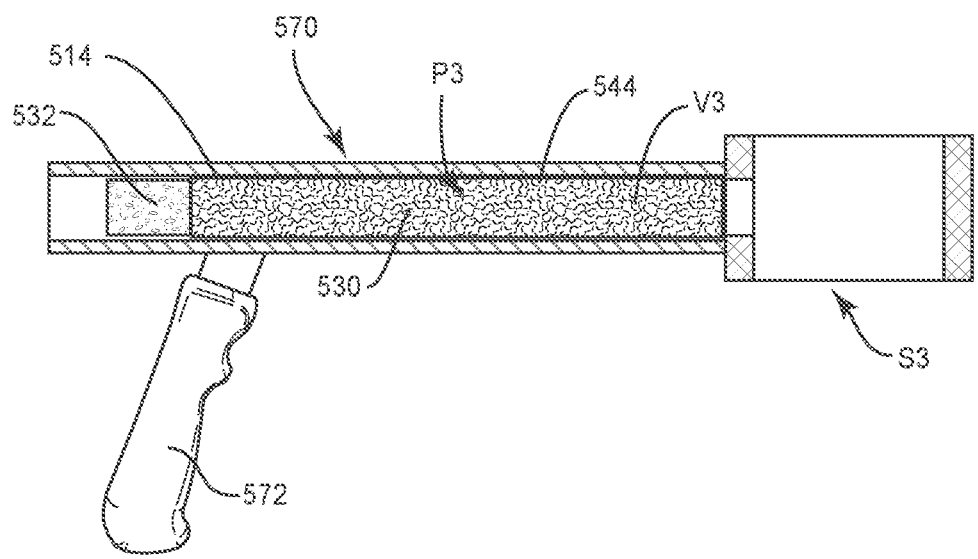
FIG. 21 is a cross section view of components of one embodiment of a surgical system in accordance with the principles of the present disclosure.
Figure 22:
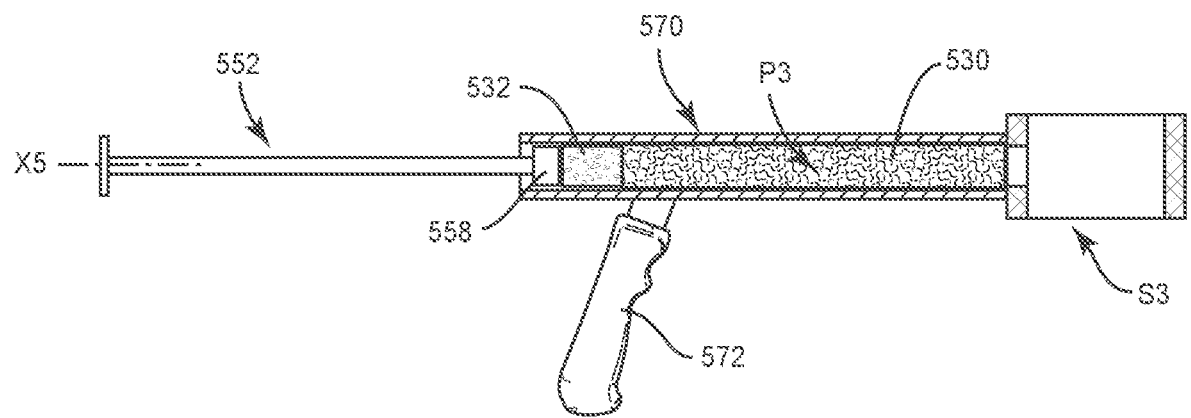
FIG. 22 is a cross section view of components of one embodiment of a surgical system in accordance with the principles of the present disclosure.
Figure 23:
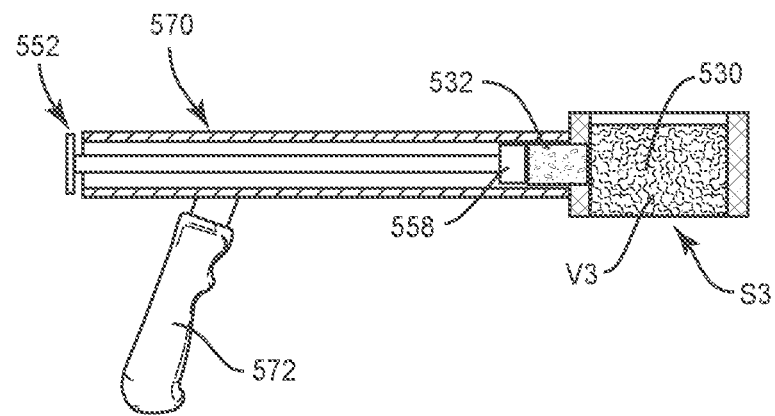
FIG. 23 is a cross section view of the components shown in FIG. 22.

In some embodiments, an inserter 370 including a cannula for disposal of surgical injection device 512 is employed to facilitate connection with selected site S3, as shown in FIGS. 21-23. In some embodiments, inserter 570 includes a handle 572 configured to facilitate manipulation and positioning of surgical injection device 512.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical injection device comprising:
at least one tubular element defining a passageway configured for disposal of a selected volume of an agent and an evacuator disposed within the passageway;
a first plunger engageable with the agent; and
an actuator comprising a second plunger engageable with the evacuator to entirely expel the selected volume of the agent from the passageway to a selected site, wherein the evacuator includes a stopper configured for axial translation relative to the at least one tubular element, wherein the stopper is implantable with the selected site.

2. A surgical injection device as recited in claim 1, wherein the agent and the evacuator are disposed in series within the passageway.

3. A surgical injection device as recited in claim 1, wherein the at least one tubular element includes a syringe and tubing connected with a distal end of the syringe.

4. A surgical injection device as recited in claim 1, wherein the agent includes a plurality of layers.

5. A surgical injection device as recited in claim 1, wherein the agent and the evacuator comprise a plurality of alternating layers.

6. A surgical injection device as recited in claim 1, wherein the agent includes a first viscosity and the evacuator includes a second viscosity lower than the first viscosity.

7. A surgical injection device as recited in claim 1, wherein the agent includes a first viscosity and the evacuator includes a second viscosity that is equal to the first viscosity.

8. A surgical injection device as recited in claim 1, wherein the at least one tubular element includes a plurality of syringes disposed in a side-by-side arrangement and tubing connected with the plurality of syringes.

9. A surgical injection device as recited in claim 8, wherein the plurality of syringes comprise a first syringe including the agent and a second syringe including the evacuator.

10. A surgical injection device as recited in claim 8, wherein the tubing includes a bifurcated extension that connects the tubing to the plurality of syringes.

11. A surgical injection device as recited in claim 8, wherein at least one of the plurality of syringes includes a one way valve.

12. A surgical injection device as recited in claim 8, wherein the tubing defines a mixing chamber that communicates with the passageway.

13. A surgical injection device as recited in claim 1, wherein the actuator includes a flange engageable with an inner surface of the at least one tubular element that resists and/or prevents separation of the actuator and the at least one tubular element.

14. A surgical injection device comprising:
a syringe barrel defining a portion of a passageway;
tubing connected with a distal end of the syringe barrel and defining another portion of the passageway;
a first plunger disposed within the syringe barrel and engageable with a bone graft;
a selected volume of bone graft and a flowable backfill disposed in series within the passageway; and
a second plunger engageable with the evacuator such that the evacuator engages the backfill to entirely expel the selected volume of the bone graft from the passageway to a void of a selected site, wherein the evacuator includes a stopper configured for axial translation relative to the at least one tubular element, wherein the stopper is implantable with the selected site.

15. A surgical system comprising:
at least one tubular element defining a passageway;
a selected volume of bone graft and an evacuator disposed within the passageway,
a first plunger being engageable with the selected volume of bone graft;
an actuator; and
an interbody implant defining a void,
the actuator comprising a second plunger being engageable with the evacuator to entirely expel the selected volume of the bone graft from the passageway to the void, wherein the evacuator includes a stopper configured for axial translation relative to the at least one tubular element, wherein the stopper is implantable with the selected site.

16. A surgical system as recited in claim 15, wherein the at least one tubular element is pre-filled with the bone graft.

\* \* \* \* \*